United States Patent
Minamio et al.

(10) Patent No.: US 9,907,877 B2
(45) Date of Patent: Mar. 6, 2018

(54) SANITIZATION MIST SHOWER APPARATUS

(71) Applicant: Panasonic Intellectual Property Management Co., Ltd., Osaka (JP)

(72) Inventors: Masanori Minamio, Osaka (JP); Akira Isomi, Osaka (JP); Daisuke Tabata, Osaka (JP); Yukiko Kitahara, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 13 days.

(21) Appl. No.: 15/099,335

(22) Filed: Apr. 14, 2016

(65) Prior Publication Data

US 2016/0361454 A1   Dec. 15, 2016

(30) Foreign Application Priority Data

Jun. 9, 2015   (JP) .................................. 2015-116869

(51) Int. Cl.
*A61L 9/14* (2006.01)
*B05B 7/24* (2006.01)
(Continued)

(52) U.S. Cl.
CPC ................ *A61L 9/145* (2013.01); *A61L 9/14* (2013.01); *A61L 9/22* (2013.01); *B05B 7/062* (2013.01); *B05B 7/2489* (2013.01); *B05B 7/2494* (2013.01); *A61L 2/14* (2013.01); *A61L 2/18* (2013.01); *A61L 2/22* (2013.01); *A61L 2209/213* (2013.01); *B05B 7/2491* (2013.01)

(58) Field of Classification Search
CPC ..... A61L 2/14; A61L 2/18; A61L 2/22; A61L 9/14; A61L 9/145; A61L 9/22; A61L 2209/213; A47F 3/001; A47F 3/0495; B05B 1/18; B05B 1/185; B05B 7/062; B05B 7/066–7/068; B05B 7/0861; B05B 7/2489; B05B 7/2491; B05B 7/2494
USPC ................ 239/289, 366, 426, 431, 433, 434
See application file for complete search history.

(56) References Cited

U.S. PATENT DOCUMENTS 2,609,233 A * 9/1952 Stearman ............ A01M 7/0003
                                                     239/351
7,291,314 B2 * 11/2007 Paskalov .................. A61L 2/18
                                                     205/742
(Continued)

FOREIGN PATENT DOCUMENTS

JP   2006-109924   4/2006
JP   2010-247133   11/2010
(Continued)

*Primary Examiner* — Arthur O Hall
*Assistant Examiner* — Cody Lieuwen
(74) *Attorney, Agent, or Firm* — Panasonic IP Management; Kerry S. Culpepper

(57) ABSTRACT

A sanitization mist shower apparatus includes a water tank that stores water, a plasma generator that causes a plasma discharge in water inside the water tank and generates reformed water, an air blower that blows pressurized air, and a mist nozzle that spouts fine mist obtained by mixing the reformed water supplied from the water tank and the pressurized air supplied from the air blower. A liquid pressure of the reformed water supplied to the mist nozzle and air pressure of the pressurized air are substantially the same as each other.

4 Claims, 13 Drawing Sheets

(51) Int. Cl.
*A61L 9/22* (2006.01)
*B05B 7/06* (2006.01)
*A61L 2/14* (2006.01)
*A61L 2/18* (2006.01)
*A61L 2/22* (2006.01)

(56) References Cited

U.S. PATENT DOCUMENTS

| | | | |
|---|---|---|---|
| 2003/0035754 A1 * | 2/2003 | Sias | A61L 2/14 422/29 |
| 2011/0284042 A1 | 11/2011 | Goessens | |
| 2013/0098880 A1 | 4/2013 | Korolev et al. | |
| 2013/0272929 A1 * | 10/2013 | Pelfrey | A61L 2/14 422/186.04 |
| 2014/0322096 A1 | 10/2014 | Pelfrey et al. | |

FOREIGN PATENT DOCUMENTS

| | | | |
|---|---|---|---|
| JP | 2011-087905 | | 5/2011 |
| JP | 2012-075487 | | 4/2012 |
| JP | 2012075487 A | * | 4/2012 |
| JP | 2012-516743 | | 7/2012 |
| JP | 2015-093864 | | 5/2015 |

* cited by examiner

SANITIZATION MIST SHOWER APPARATUS

TECHNICAL FIELD

The technical field relates to a sanitization mist shower apparatus which is able to eliminate bacteria and the like in the air.

BACKGROUND

In the related art, an air sanitization apparatus has been proposed. According to the air sanitization apparatus, in grocery product factories, food factories, and the like, water, such as tap water including chlorine ions, is subjected to electrolysis, the electrolyzed water including hypochlorous acid is generated, the electrolyzed water is mixed with the pressurized air, and the mixture thereof is sprayed indoors so that the electrolyzed mist is brought into contact with bacteria included in the air in a room, thereby performing sanitization (for example, refer to Japanese Patent Unexamined Publication No. 2011-087905).

In addition, a sanitization apparatus has been proposed. According to the sanitization apparatus, a discharge unit is provided inside a storage tank storing water, hydrogen peroxide water is generated in the water by causing a streamer discharge, and the water is sprayed indoors through a spray nozzle (for example, refer to Japanese Patent Unexamined Publication No. 2012-075487).

SUMMARY

Japanese Patent Unexamined Publication No. 2011-087905 discloses the air sanitization apparatus which uses electrolyzed water including hypochlorous acid obtained by causing water, such as tap water including chlorine ions, to be subjected to electrolysis. Accordingly, minerals (calcium and magnesium) and hypochlorous acid in the tap water are combined together and become slurry and are crystallized in forms of calcium hydroxide and magnesium hydroxide, thereby adhering to a nozzle. Thus, it is difficult to use the apparatus for a long period of time.

Japanese Patent Unexamined Publication No. 2012-075487 discloses the sanitization apparatus which uses reformed water including hydrogen peroxide water. Accordingly, there is no clogging caused in the nozzle. However, since the reformed water is pressurized by using a pump and the pressurized reformed water is sprayed indoors through a spray nozzle, the particle size of the reformed water to be sprayed becomes large so that the sprayed water does not scatter in the air. Thus, it becomes difficult to perform air sanitization in a large space such as a grocery product factory.

Accordingly, a sanitization mist shower apparatus is provided in which the particle size of reformed water to be sprayed can be reduced and air sanitization in a large space such as a grocery product factory and a food factory can be performed.

According to an aspect, a sanitization mist shower apparatus includes a water tank that stores water, a plasma generator that causes a plasma discharge in water inside the water tank and generates reformed water, a mist nozzle that spouts fine mist through a mist spout port, an air blower that supplies pressurized air obtained by pressurizing air to the mist nozzle, and a liquid pressurizer that pressurizes the reformed water generated by the plasma generator inside the water tank and supplies the pressurized reformed water to the mist nozzle. The fine mist is generated in the mist nozzle by mixing the pressurized air supplied from the air blower and the reformed water supplied from the liquid pressurizer and the fine mist is spouted through the mist spout port. Air pressure of the pressurized air supplied to the mist nozzle and liquid pressure of the reformed water are substantially the same as each other.

According to the aspect, the sanitization mist shower apparatus has a configuration in which in a state where the air pressure of the pressurized air supplied to the mist nozzle and the liquid pressure of the reformed water are substantially the same as each other, the reformed water which includes OH radicals having a high sterilization effect is generated, the reformed water is mixed with the pressurized air, and the fine mist having a small particle size is sprayed by the gas-liquid mixing nozzle. According to such a configuration, the particle size of the fine mist to be sprayed can be reduced, the fine mist can scatter in the air, and air sanitization in a large space such as a grocery product factory and a food factory can be performed.

BRIEF DESCRIPTION OF THE DRAWINGS

FIG. 1 is a configuration diagram illustrating an example of a sanitization mist shower apparatus of a first embodiment.

FIG. 2 is a view illustrating the appearance of an example of a mist nozzle of the first embodiment.

FIG. 3 is a cross-sectional view illustrating the mist nozzle taken along line 3-3 in FIG. 2.

FIG. 4 is an end view illustrating a cross section of the mist nozzle taken along line 4-4 in FIG. 3.

FIG. 5 is a cross-sectional view of an air orifice section in a comparative example provided with two air orifice flow channels.

FIG. 6 is a cross-sectional view of the air orifice section in another comparative example provided with four air orifice flow channels.

FIG. 7 is a cross-sectional view of the air orifice section in further another comparative example provided with eight air orifice flow channels.

FIG. 8 is a graph illustrating a relationship among air pressure PA, liquid pressure PW, and the average particle size.

FIG. 9 is a graph of a result of a comparative experiment in which air pressure PA and liquid pressure PW are substantially the same as each other, and the number of air orifice flow channels varies.

FIG. 10 is another graph of the result of the comparative experiment in which air pressure PA and liquid pressure PW are substantially the same as each other, and the number of air orifice flow channels varies.

FIG. 11 is a graph of a result of a comparative experiment in which temporal changes of the indoor floating bacteria count are measured in a case where the sanitization mist shower apparatus of the first embodiment is used.

FIG. 12 is a configuration diagram illustrating an example of a sanitization mist shower apparatus of a second embodiment.

FIG. 13 is a graph of a result of a comparative experiment in which temporal changes of the indoor floating bacteria count are measured in a case where the sanitization mist shower apparatus of the second embodiment is used.

DETAILED DESCRIPTION OF PREFERRED EMBODIMENTS

Hereinafter, various exemplary embodiments will be described with reference to the drawings.

First Embodiment

Configuration of Sanitization Mist Shower Apparatus

Figure 1:
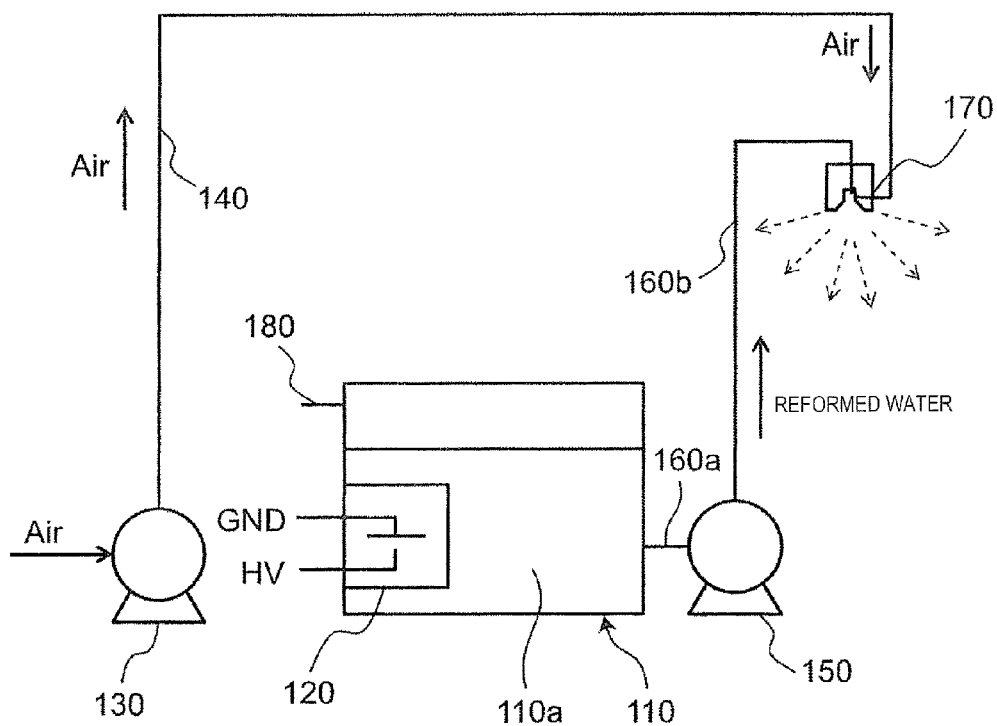

FIG. 1 is a configuration diagram illustrating an example of sanitization mist shower apparatus 100 according to a first embodiment.

Sanitization mist shower apparatus 100 according to the first embodiment of the present invention includes water tank 110, plasma generator 120, liquid pressurizer 150, mist nozzle 170, air blower 130, and first gas pipe 140.

Water tank 110 is a sealed container and is connected to liquid pressurizer 150 by first liquid delivery pipe 160a. Water feed pipe 180 is provided on the top of water tank 110, and water such as tap water is supplied to the inside of water tank 110 through water feed pipe 130.

Plasma generator 120 includes two electrodes (not illustrated) arranged in water 110a in water tank 110, and a power source unit (not illustrated) applying voltages to the electrodes. When the power source unit applies a voltage between the two electrodes arranged so as to face each other in the water inside water tank 110, air bubbles are formed in the vicinity of the electrodes and a streamer discharge occurs in the air bubbles, resulting in insulation breakdown of the water. Thus, plasma can be generated. The plasma generated in the water causes dissociation reaction of water, and thus, OH radicals are generated. The OH radicals generated in the water have high oxidation-reduction potential and have extremely strong oxidation power. Therefore, various bacteria included in the water can be decomposed and eliminated. When OH radicals are generated in the water, hydrogen peroxide is generated as a byproduct thereof due to recombination reaction among the OH radicals. Hydrogen peroxide is a type of active oxygen having relatively high oxidation power and has a function of sterilization. A small inducement such as irradiation of ultraviolet rays makes hydrogen peroxide easily generate OH radicals having strong oxidation power.

According to such a configuration, plasma generator 120 generates OH radicals and hydrogen peroxide in the water in water tank 110. As a result, water inside water tank 110 is sterilized and reformed water having a high sterilization effect is generated.

Liquid pressurizer 150 is connected to water tank 110 via first liquid delivery pipe 160a and is connected to mist nozzle 170 via second liquid delivery pipe 160b. For example, liquid pressurizer 150 is configured to have a pump causing reformed water supplied from water tank 110 to be pressure-fed to mist nozzle 170, a motor driving the pump, and a flow rate control valve controlling the flow rate of the reformed water pressure-fed from the pump. For example, the revolution speed of the motor (not illustrated) or the opening degree of the flow rate control valve (not illustrated) is controlled so that the output pressure or the flow rate of the reformed water to be sent from liquid pressurizer 150 to second liquid delivery pipe 160b is controlled.

Air blower 130 is connected to mist nozzle 170 via first gas pipe 140, and supplies air from air blower 130 to mist nozzle 170. For example, air blower 130 is configured to have a compressor, a motor driving the compressor, and a flow rate control valve controlling the flow rate of pressurized air pressurized in the compressor. The pressurized air pressurized by air blower 130 is supplied to mist nozzle 170 via first gas pipe 140. For example, the revolution speed of the motor (not illustrated) or the opening degree of the flow rate control valve (not illustrated) is controlled so that the output pressure or the flow rate of the pressurized air to be sent from air blower 130 to first gas pipe 140 is controlled.

Structure of Mist Nozzle

Figure 2:
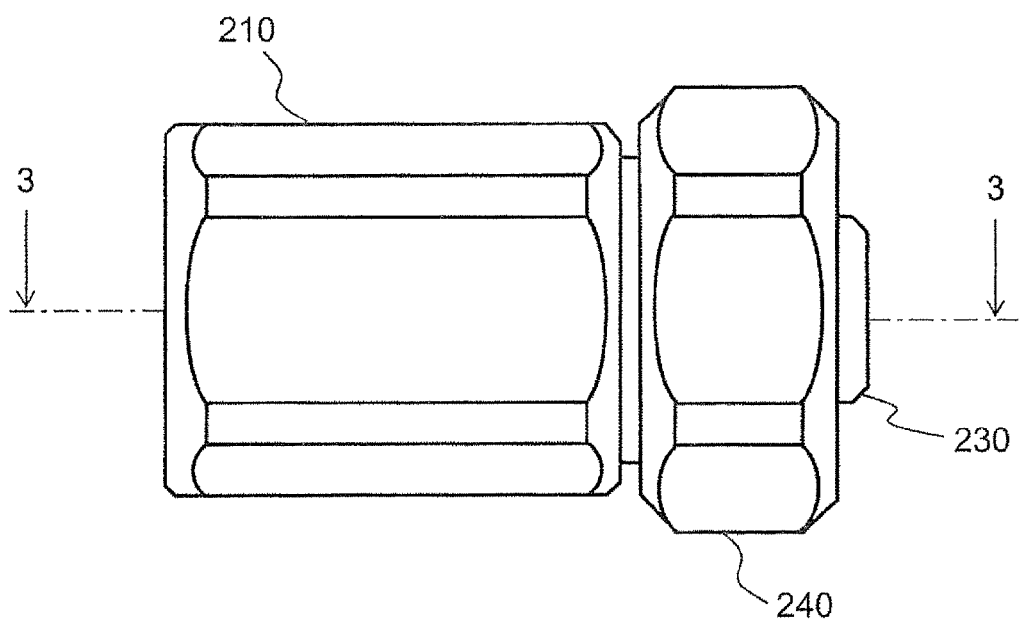
Figure 3:
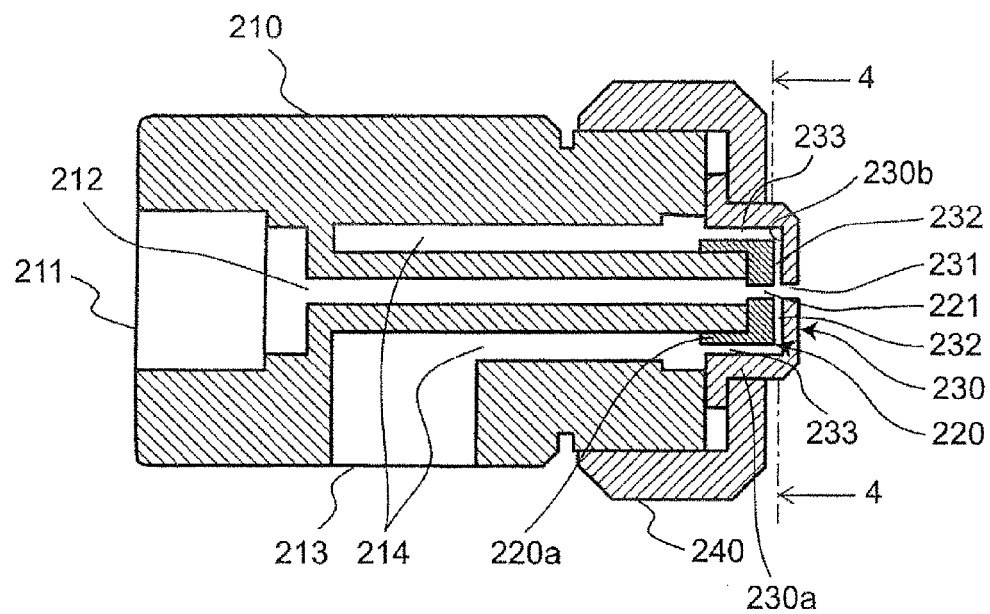
Figure 4:
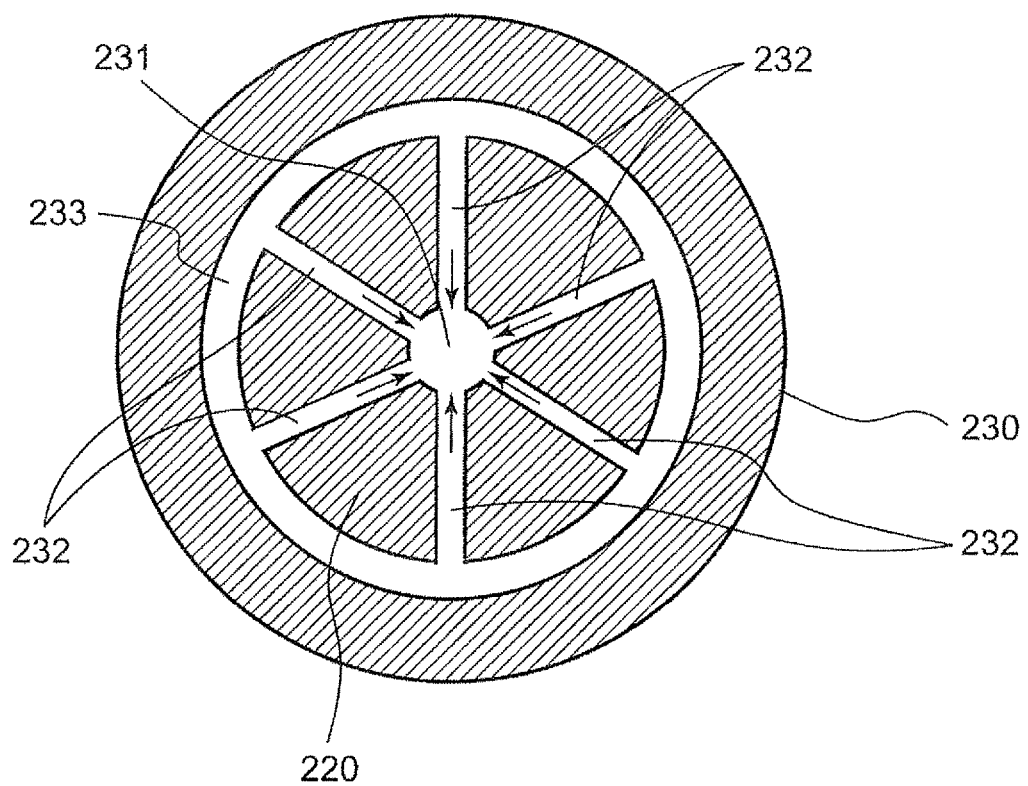

FIG. 2 is a view illustrating the appearance of an example of mist nozzle 170 of sanitization mist shower apparatus 100 of the first embodiment. FIG. 3 is a cross-sectional view illustrating mist nozzle 170 taken along line 3-3 in FIG. 2. FIG. 4 is an end view illustrating a cross section of mist nozzle 170 taken along line 4-4 in FIG. 3.

As illustrated in FIGS. 2 and 3, mist nozzle 170 is configured to have nozzle main body 210, water orifice component 220, air orifice component 230, and cap component 240. In nozzle main body 210, liquid flow channel 212 is formed along the central axis from the rear end side (the left end side in FIG. 3) of nozzle main body 210 to the tip spouting side (the right end side in FIG. 3). Liquid flow channel entrance 211 is provided at the rear end of nozzle main body 210 of liquid flow channel 212. Liquid flow channel entrance 211 is connected to second liquid delivery pipe 160b. Gas flow channel 214 is formed in nozzle main body 210 so as to be parallel to liquid flow channel 212, and nozzle main body 210 is connected to first gas pipe 140 via gas flow channel entrance 213 provided on the side surface. As an example, tubular gas flow channel 214 is formed in the periphery of liquid flow channel 212.

Screw sections (not illustrated) for screwing nozzle main body 210 and cap component 240 together are respectively formed on the inner circumferential surface of a tubular section of cap component 240 and the outer circumferential surface of a tip section of nozzle main body 210. Water orifice component 220 is connected to the tip of nozzle main body 210, and air orifice component 230 is installed so as to cover water orifice component 220. In this state, cap component 240 is screwed and fitted to the tip section of nozzle main body 210, and thus, nozzle main body 210, water orifice component 220, air orifice component 230, and cap component 240 are integrally fixed. Circular opening 221 communicating with liquid flow channel 212 and spouting reformed water is provided at the center of water orifice component 220. Reformed water pressurized by liquid pressurizer 150 flows in through liquid flow channel entrance 211 to liquid flow channel 212 and is spouted through opening 221 of water orifice component 220 connected to nozzle main body 210.

As illustrated in FIG. 4, mist spout port 231 penetrating in the axial direction is provided at air orifice component 230. Recessed grooves are formed on surface 230b being in contact with water orifice component 220 of air orifice component 230 at radially equal intervals from the center of air orifice component 230. Water orifice component 220 and air orifice component 230 are in contact with and are fixed to each other so that the recessed grooves are sealed and air orifice flow channels 232 are formed. Annular gas flow channel 233 formed between tubular section 220a of water orifice component 220 and tubular section 230a of air orifice component 230 communicates with air orifice flow channels 232. Therefore, pressurized air that flows in through gas flow channel entrance 213 can flow into all air orifice flow channels 232 at equal air pressure via gas flow channel 214 and annular gas flow channel 233. Here, six air orifice flow channels 232 are provided in the first embodiment. However, the configuration is acceptable as long as six or more air orifice flow channels 232 are provided. The reason thereof will be described later. The shape of a cross section of each recessed groove formed in air orifice component 230 may be a polygonal shape or a semicircular shape.

By having such a configuration, streams of air spouted through all air orifice flow channels 232 of air orifice component 230 collide with each other on the central axis of air orifice component 230. Air orifice flow channels 232 are formed on a plane on a spouting side of water orifice component 220. Therefore, the streams of air collide with each other on a plane substantially parallel to the plane. Meanwhile, reformed water is spouted through opening 221 of water orifice component 220 along a direction substantially perpendicular to the plane on the spouting side of water orifice component 220. Accordingly, in the substantially perpendicular direction, the reformed water collides with a collision section where streams of pressurized air spouted through air orifice flow channels 232 collide with each other. Then, the reformed water is mixed with the pressurized air in the collision section, thereby becoming fine mist. The fine mist generated in such a manner is sprayed through mist spout port 231 of air orifice component 230.

Mist spout port 231 may have a tapered structure of being increased in diameter in the spouting direction. Accordingly, fine mist can be sprayed through mist spout port 231 at a wide angle so that a probability of collision of mists is reduced and recombination of the mists can be prevented. Thus, it is possible to prevent the mist from increasing in average particle size.

Example

Subsequently, a result of a comparative experiment will be described. The comparative experiment was performed in order to check an effect of sanitization mist shower apparatus 100 of the first embodiment of the present invention.

Figure 5:
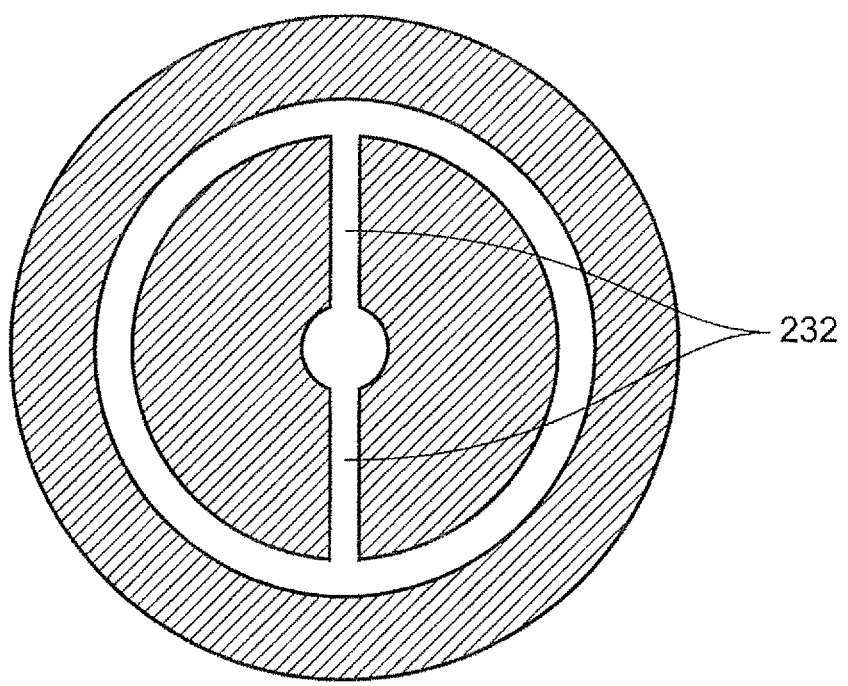
Figure 6:
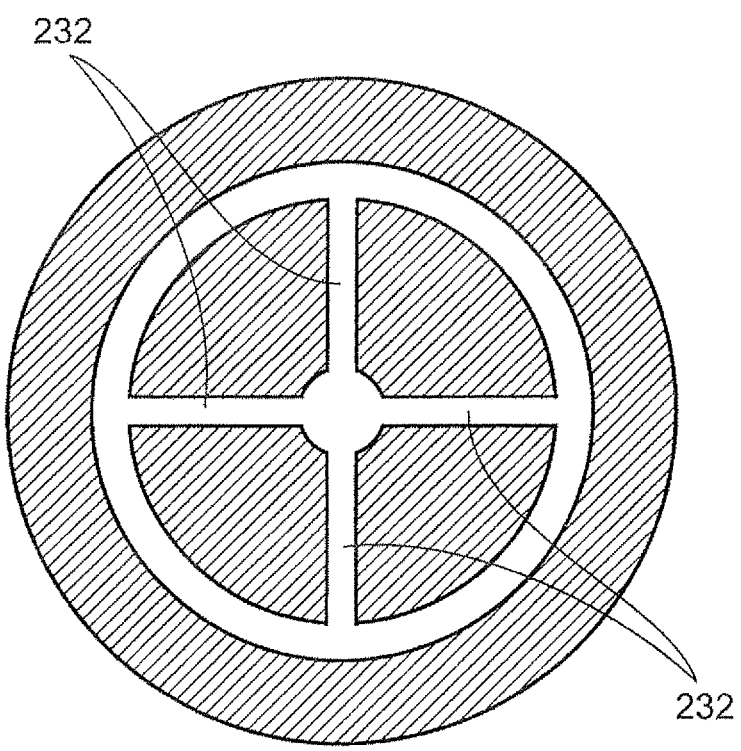
Figure 7:
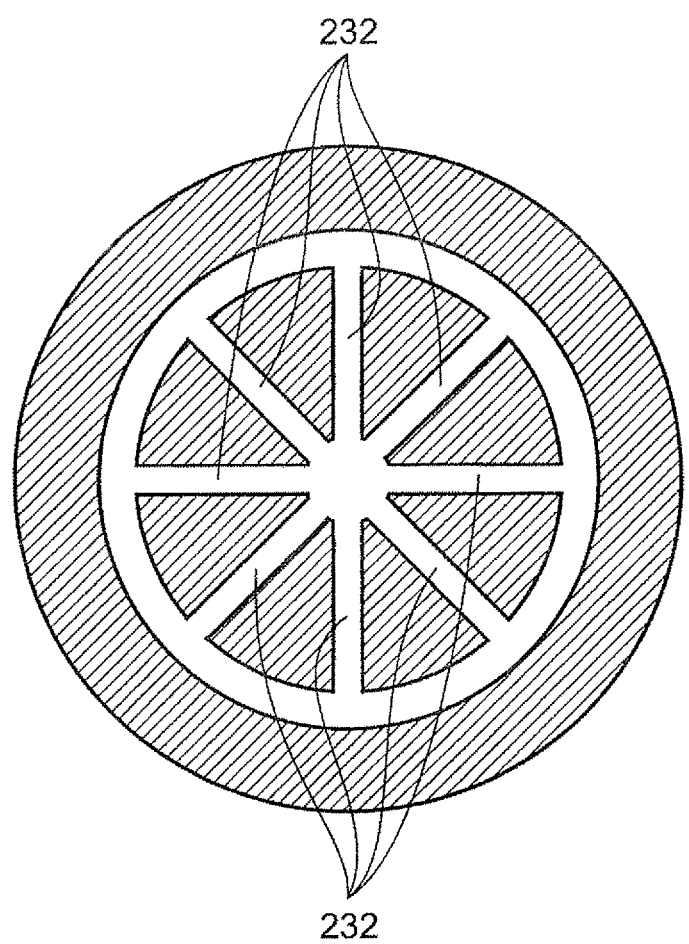

First, evaluation of Sauter average particle size and unevenness of particle sizes in mist nozzle 170 of the first embodiment was performed. Each air orifice flow channel 232 of air orifice component 230 of mist nozzle 170 had a rectangular cross section and had the width of 0.7 mm and the depth of 0.25 mm. The diameter of mist spout port 231 of air orifice component 230 was 1.0 mm. The diameter of opening 221 of water orifice component 220 was 0.7 mm. Air pressure PA of the pressurized air and liquid pressure PW were respectively adjusted by the compressor of air blower 130 or the pump of liquid pressurizer 150, and the flow rate of air and the flow rate of water were respectively controlled by the flow rate control valves so that the sprayed quantity ranged from 10 ml/min to 100 ml/min. In comparative examples, as illustrated in FIGS. 5 to 7, the numbers N of air orifice flow channels 232 were respectively set to two, four, and eight. The shape of a cross section of each air orifice flow channel 232 in the comparative examples, the diameter of mist spout port 231 of air orifice component 230, and the diameter of opening 221 of water orifice component 220 were the same as those in an example. The sprayed quantities in the comparative examples were substantially the same as those in the example.

Figure 8:
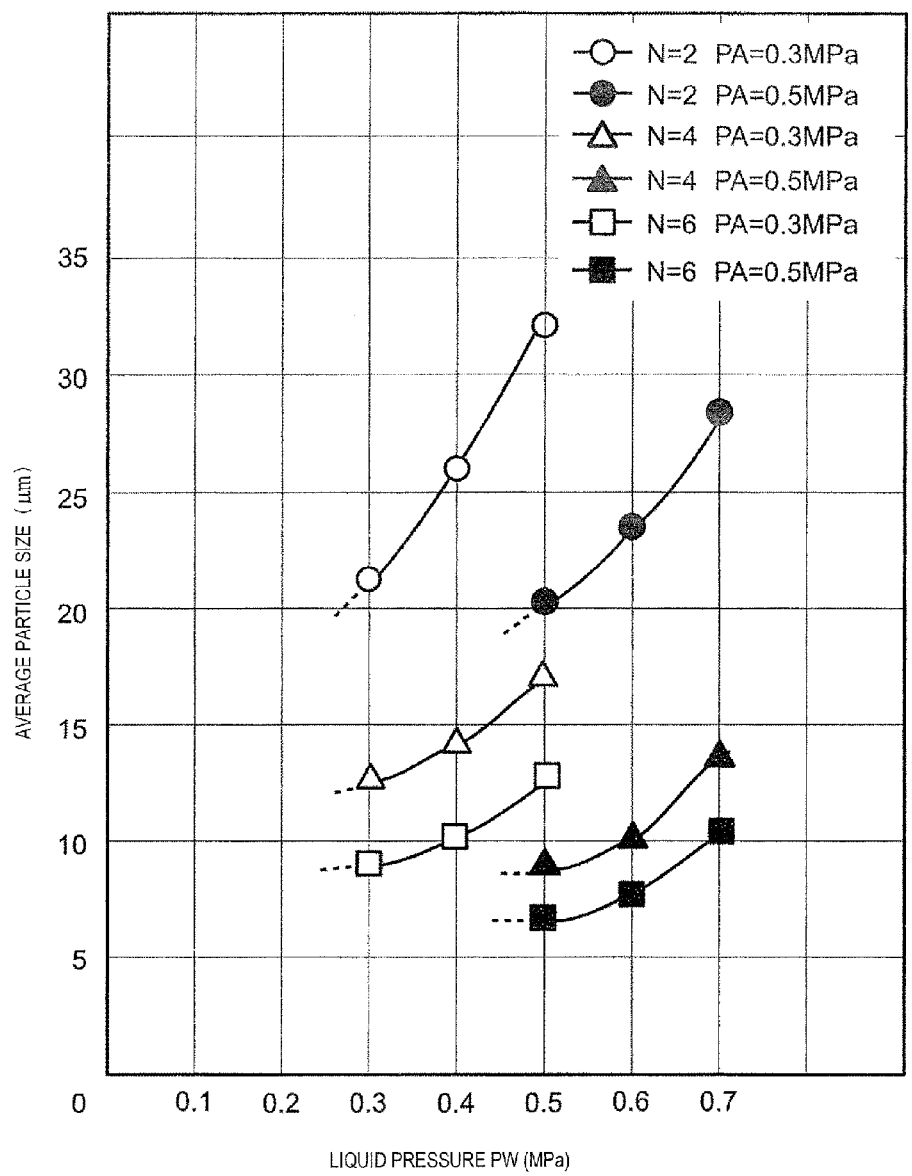

FIG. 8 is a view illustrating a relationship among air pressure PA, liquid pressure PW, and the average particle size. Here, as the average particle size, the Sauter average particle size measured by applying a laser diffraction method at a location which was separated by 30 cm from an external surface on the spouting side of air orifice component 230 on the central axis of mist nozzle 170 was adopted. As illustrated in FIG. 8, in a case where air pressure PA and liquid pressure PW were substantially the same as each other in all cases where the number N of air orifice flow channels 232 was two, four, and six, a result of the minimum average particle size was obtained. Here, the expression "substantially the same" denotes a case where when air pressure PA is X pascals, liquid pressure PW ranges from 0.8X pascals to 1.2X pascals, and more preferably denotes a case where liquid pressure PW ranges from 0.9X pascals to 1.1X pascals. In a region where liquid pressure PW fell below gas pressure PA, liquid could not be output so that mist could not be sprayed.

Figure 9:
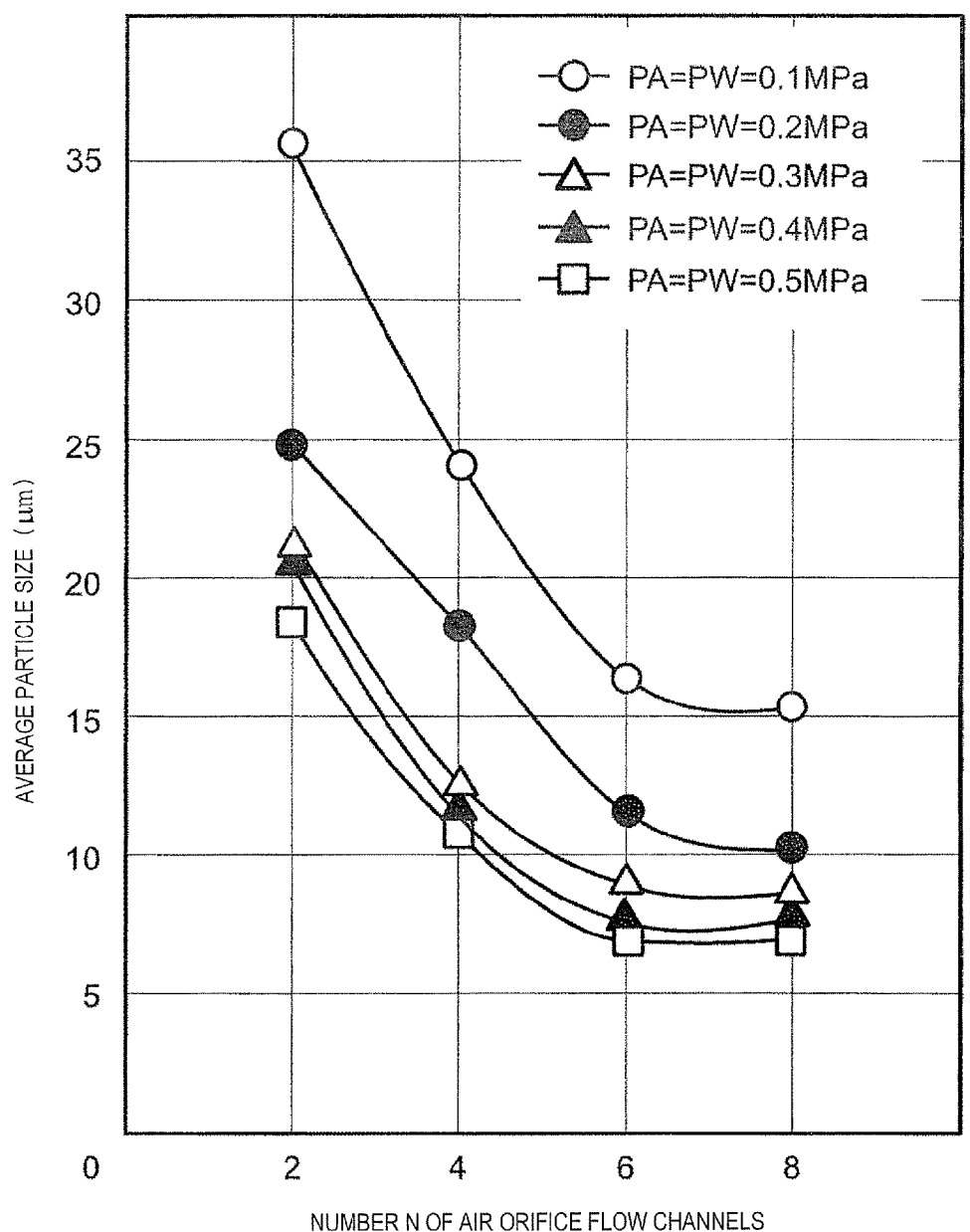
Figure 10:
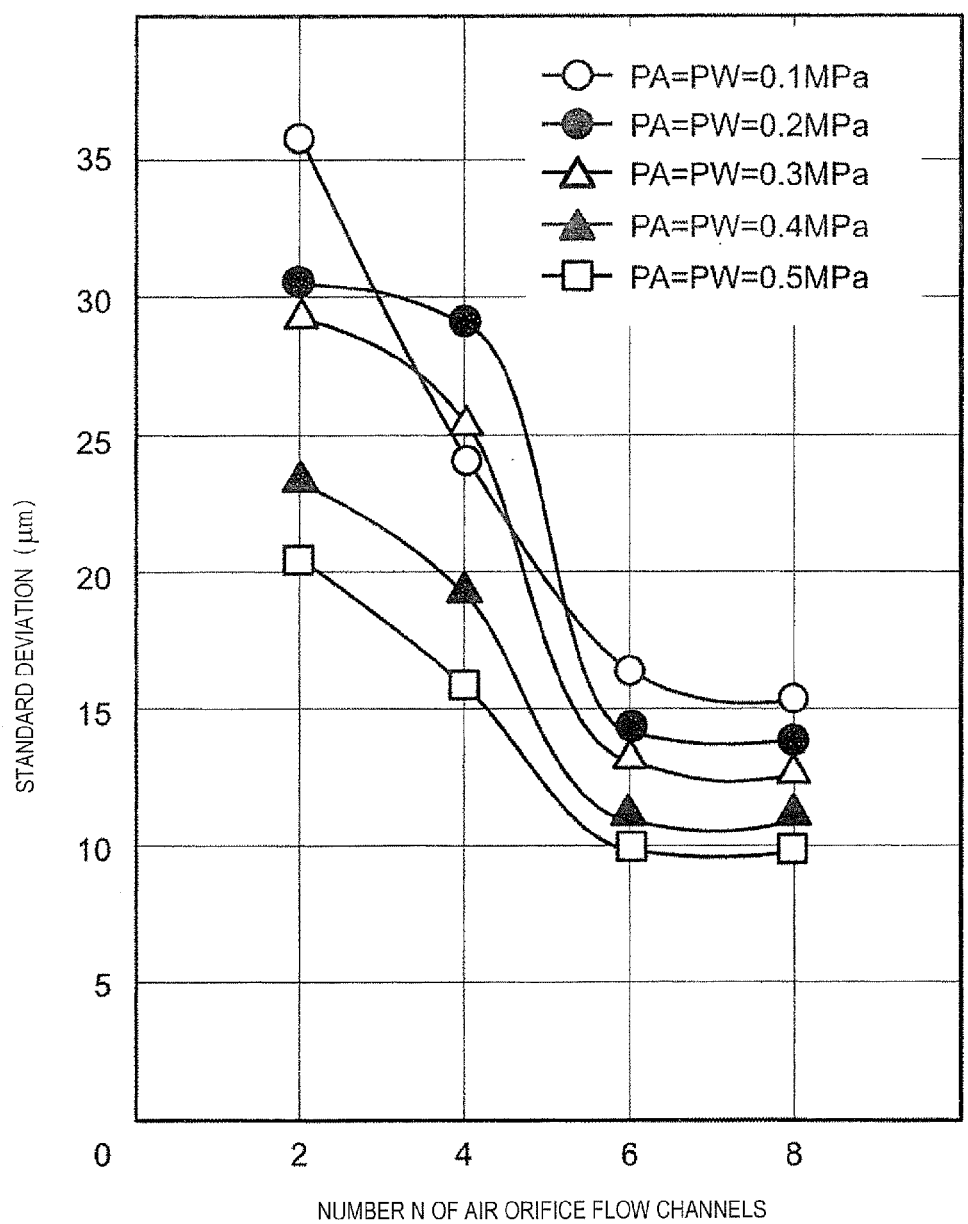

FIGS. 9 and 10 are results of the comparative experiment in which air pressure PA and liquid pressure PW are substantially the same and the number N of air orifice flow channels 232 varies.

As illustrated in FIG. 9, in a case where air pressure PA was 0.3 MPa or greater and the number of air orifice flow channels 232 was six or more, it was possible to check that the average particle size became 10 μm or smaller. In a case where mist having particle sizes exceeding 10 μm adhered to a human body, the external surface of skin became wet, resulting in a problem of an unpleasant feeling. Therefore, it is preferable that the number of air orifice flow channels 232 is six or more. There is no particular regulation regarding the upper limit of the number thereof. However, as the number thereof is increased, the width of air orifice flow channels 232 becomes narrow and the flow rate of air is decreased. Therefore, it is preferable that the number thereof is ten or less. In a viewpoint of fine particles, air pressure FA is preferably 0.3 MPa or greater.

As illustrated in FIG. 10, a standard deviation indicating unevenness of the particle size became significant in a case where the number of air orifice flow channels 232 was four or less so that it was difficult to manage the particle size.

Figure 11:
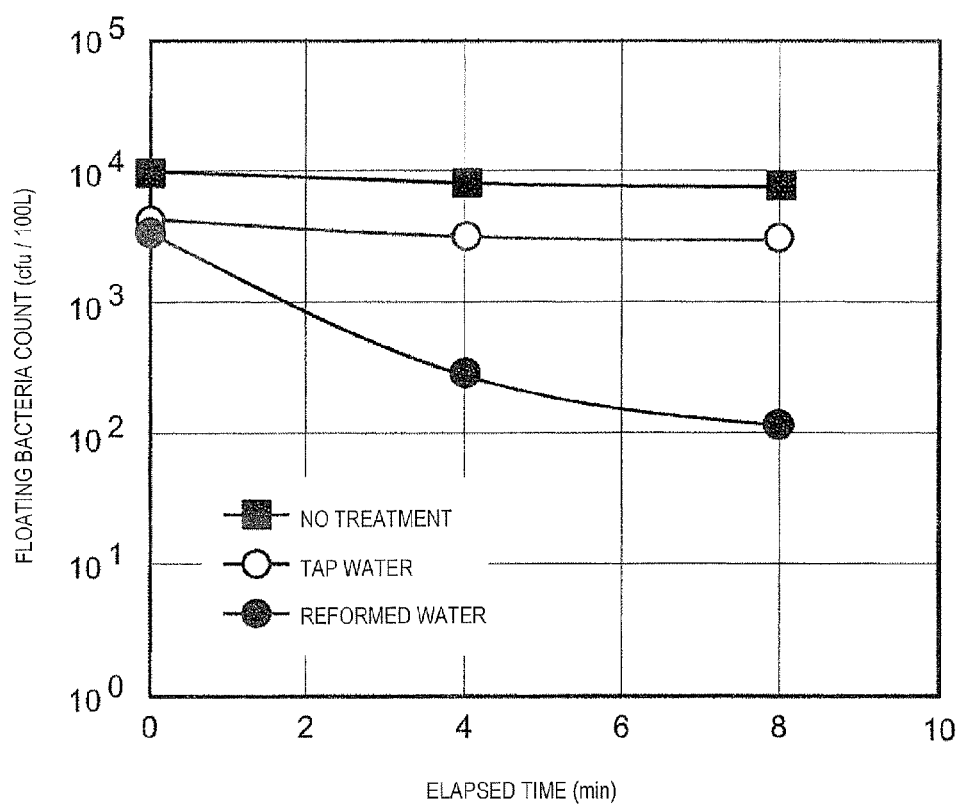

Subsequently, an operational effect of sanitization mist shower apparatus 100 according to the first embodiment will be described. FIG. 11 is a result of a comparative experiment in which temporal changes of the indoor floating bacteria count are measured in a case where the sanitization mist shower apparatus of the first embodiment is used. The number of air orifice flow channels 232 was six, the air pressure and the liquid pressure were 0.4 MPa, and the sprayed quantity was controlled to be 50 ml/min. In FIG. 11, the data of "no treatment" indicates the floating bacteria count in a case where sanitization mist shower apparatus 100 is not in operation. The data of "tap water" indicates the floating bacteria count in a case where tap water is sprayed without operating plasma generator 120 of sanitization mist shower apparatus 100. As illustrated in FIG. 11, in cases of no treatment and tap water, there is no reduction of the floating bacteria count which occurs due to the elapse of time.

In contrast, in a case where plasma generator 120 is in operation, the floating bacteria count is reduced, and thus, it has been ascertained that plasma generator 120 has an extremely high-level function of sterilization.

Therefore, according to the first embodiment, fine mist (mist of reformed water) is generated from reformed water which includes OH radicals having a high sterilization effect, the fine mist is sprayed, and air pressure PA of the pressurized air supplied to mist nozzle 110 and liquid pressure PW of the reformed water are substantially the same as each other. Thus, the average particle size of the fine mist can be minimized. Moreover, the particle size of the reformed water to be sprayed can be reduced. Therefore, the reformed water can scatter in the air, and air sanitization in a large space such as a grocery product factory and a food factory can be performed. Since the fine mist is generated by using the reformed water, the apparatus can be used for a long period of time without causing clogging of the nozzle.

According to the configuration of the first embodiment in which the average particle size of the fine mist of the reformed water to be sprayed is 10 μm or smaller by causing air pressure PA to be 0.3 MPa or greater and the number of air orifice flow channels 232 to be six or more, and an air current spouted through air orifice flow channels 232 collides with a liquid current in perpendicular directions, mist having a small particle size can be evenly spouted. Therefore, a human body does not become wet in a case where sprayed mist adheres to the human body, thereby not causing an unpleasant feeling.

Second Embodiment

In the first embodiment, water tank 110 and mist nozzle 170 are connected to each other through second liquid delivery pipe 160b via liquid pressurizer 150. In a second embodiment, description will be given regarding a configuration in which liquid pressurizer 150 is not arranged, water tank 110 and mist nozzle 170 are directly connected to each other through third liquid delivery pipe 360, and air blower 130 and water tank 110 are connected to each other through second gas pipe 340.

Figure 12:
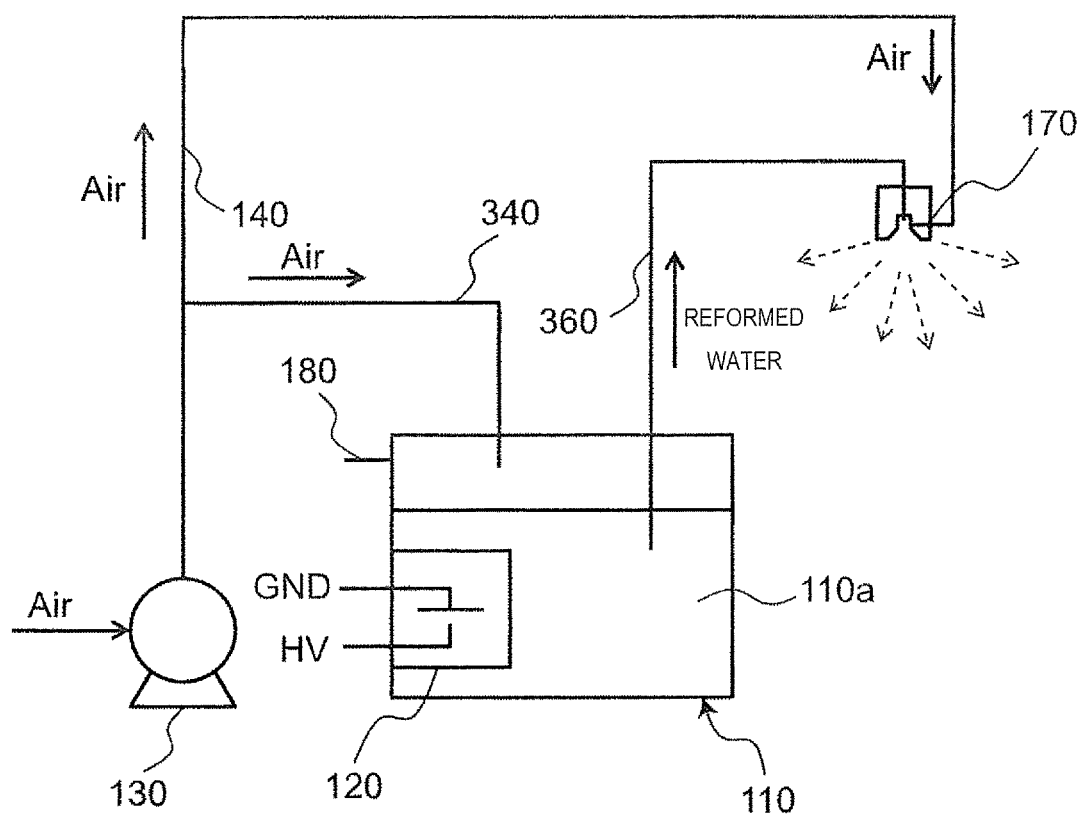

FIG. 12 is a configuration diagram illustrating an example of sanitization mist shower apparatus 300 according to the second embodiment.

Sanitization mist shower apparatus 300 according to the second embodiment includes water tank 110, plasma generator 120, mist nozzle 170, air blower 130, first gas pipe 140, and second gas pipe 340.

Mist nozzle 170 leads to water inside water tank 110 through third liquid delivery pipe 360. Air blower 130 and mist nozzle 170 are connected to each ether through first gas pipe 140. Second gas pipe 340 is bifurcated from first gas pipe 140 and is connected to water tank 110.

The configurations of plasma generator 120, mist nozzle 170, and air blower 130 are the same as those in the first embodiment. Therefore, detailed description thereof will not be repeated.

As illustrated in FIG. 12, first gas pipe 140 is bifurcated between air blower 130 and mist nozzle 170, and bifurcated second gas pipe 340 is connected to the top of water tank 110 so as to communicate therewith. Pressurized air pressurized by air blower 130 is supplied to the top of water tank 110 via second gas pipe 340. Water tank 110 has a sealed structure. Therefore, reformed water inside water tank 110 is pushed out by the pressurized air that flows into water tank 110 and is supplied to mist nozzle 170 via third liquid delivery pipe 360.

According to such a configuration, liquid pressurizer 150 can be omitted. Therefore, equipment cost can be reduced. In other words, the liquid pressurizer is configured to have air blower 130 and second gas pipe 340, which is bifurcated from first gas pipe 140, connecting air blower 130 and mist nozzle 170, and communicates with water tank 110. The liquid pressurizer has a configuration in which reformed water inside water tank 110 is pressurized by pressurized air supplied from air blower 130 to water tank 110 via second gas pipe 340, and is supplied to mist nozzle 170. Accordingly, it is possible to eliminate the necessity of separately providing a specific member as the liquid pressurizer.

Reformed water generated by using plasma generator 120 inside water tank 110 is directly supplied to mist nozzle 170 without passing through the liquid pressurizer. Therefore, the reformed water is unlikely to be influenced by agitation caused by the liquid pressurizer, or heat generated by a liquid delivery pump. Thus, it is possible to reduce the decomposition speed of hydrogen peroxide included in the reformed water.

In order to monitor whether or not the pressurization state of water tank 110 is appropriate and to prevent a reverse flow from water tank 110, a flow meter, a valve, a pressure gauge, and the like (not illustrated) may be arranged in second gas pipe 340.

It is preferable that the inner diameter of second gas pipe 340 is greater than the inner diameter of first gas pipe 140. According to such a configuration, the inside of water tank 110 can be promptly and reliably pressurized.

Example

Figure 13:
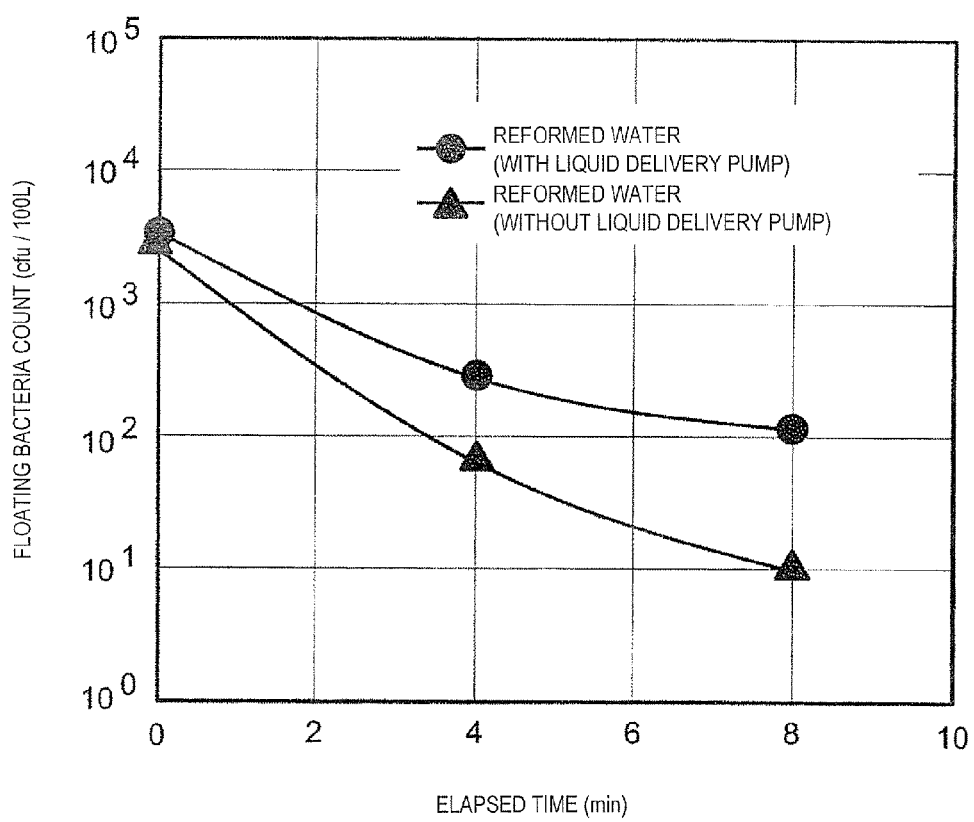

Subsequently, a result of a comparative experiment will be described. The comparative experiment was performed in order to check an effect of sanitization mist shower apparatus 300 of the second embodiment. FIG. 13 is the result of the comparative experiment in which temporal changes of the indoor floating bacteria count are measured in a case where sanitization mist shower apparatus 300 of the second embodiment is used. The number of air orifice flow channels 232 was six, the air pressure was 0.4 MPa, and the sprayed quantity was controlled to be 50 ml/min. As is clear from FIG. 13, in a case where no liquid pressurizer is used, compared to a case where a liquid pressurizer is used, it has been ascertained that there is significant reduction of the floating bacteria count which occurs due to the elapse of time.

According to the second embodiment, in addition to the effect of the first embodiment, the second embodiment has a configuration in which reformed water is pushed out from the inside of water tank 110 by using pressurized air. Therefore, liquid pressurizer 150 can be omitted. Thus, equipment costs can be reduced. Reformed water generated by using plasma generator 120 inside water tank 110 is directly supplied to mist nozzle 170 without passing through the liquid pressurizer. Therefore, the reformed water is unlikely to be influenced by agitation caused by the liquid pressurizer, or heat generated by a liquid delivery pump. Thus, it is possible to reduce the decomposition speed of hydrogen peroxide included in the reformed water.

An arbitrary embodiment or an arbitrary modification example in the various embodiments or modification examples described above can be suitably combined together so as to achieve each of the effects thereof. It is possible to mutually combine embodiments, to mutually combine examples, and to combine an embodiment and an example. Moreover, it is possible to mutually combine features of embodiments or examples different from each other.

According to the sanitization mist shower apparatus of the various embodiments, the particle size of reformed water to be sprayed can be reduced and air sanitization in a large space such as a grocery product factory and a food factory can be performed. Therefore, the various embodiments can be widely utilized in sanitization mist shower apparatuses for sanitizing indoor and outdoor.

What is claimed is:

1. A sanitization mist shower apparatus comprising:
   a water tank that stores water;
   a plasma generator that causes a plasma discharge in the water inside the water tank and generates reformed water;
   a mist nozzle that spouts fine mist through a mist spout port;
   an air blower that supplies pressurized air obtained by pressurizing air to the mist nozzle; and a liquid pressurizer that pressurizes the reformed water generated by the plasma generator inside the water tank and supplies the pressurized reformed water to the mist nozzle, wherein the fine mist is generated in the mist nozzle by mixing the pressurized air supplied from the air blower and the reformed water supplied from the liquid pressurizer, wherein air pressure of the pressurized air supplied to the mist nozzle and liquid pressure of the reformed water are substantially equal to each other, wherein the mist nozzle includes an opening of a water orifice component spouting the reformed water and at least six air orifice flow channels spouting the pressurized air, wherein the air pressure of the pressurized air is 0.3 MPa or greater, and wherein the air orifice flow channels are provided at radially equal intervals centering around a liquid current of the reformed water spouted through the opening of the water orifice component, and the pressurized air spouted through the air orifice flow channels collides with the liquid current in perpendicular directions and generates the fine mist.

2. The sanitization mist shower apparatus of claim 1, wherein the mist spout port is increased in diameter so as to be widened toward a spouting side.

3. The sanitization mist shower apparatus of claim 1, wherein the liquid pressurizer is a liquid delivery pump arranged in the middle of a liquid delivery pipe between the water tank and the mist nozzle.

4. The sanitization mist shower apparatus of claim 1,
wherein the liquid pressurizer includes the air blower and a second gas pipe, which is bifurcated from a first gas pipe connected to the air blower and the mist nozzle, and communicates with the water tank, and wherein the reformed water inside the water tank is pressurized by the pressurized air supplied from the air blower to the water tank via the second gas pipe, and the pressurized reformed water is supplied to the mist nozzle.

* * * * *